United States Patent [19]

Karydas et al.

[11] Patent Number: 4,647,284
[45] Date of Patent: Mar. 3, 1987

[54] SULFIDO- AND SULFO-SUBSTITUTED PERFLUOROALKYL PYROMELLITATES

[75] Inventors: Athanasios Karydas, Brooklyn; Robert A. Falk, New City, both of N.Y.

[73] Assignee: Ciba-Geigy Corporation, Ardsley, N.Y.

[21] Appl. No.: 791,817

[22] Filed: Oct. 28, 1985

[51] Int. Cl.$^4$ ...................... D06M 13/28; C07C 69/76
[52] U.S. Cl. ...................... 8/115.56; 560/87; 8/DIG. 21; 8/DIG. 4; 252/8.6; 252/8.7
[58] Field of Search .......................... 560/87; 8/115.61

[56] References Cited

U.S. PATENT DOCUMENTS

| | | | |
|---|---|---|---|
| 4,192,754 | 3/1980 | Marshall et al. | 560/87 |
| 4,209,610 | 6/1980 | Mares et al. | 106/2 |
| 4,283,292 | 11/1981 | Marshall et al. | 252/8.6 |
| 4,317,736 | 3/1982 | Marshall et al. | 428/395 |

Primary Examiner—Prince E. Willis
Assistant Examiner—John F. McNally
Attorney, Agent, or Firm—Michael W. Glynn; Irving M. Fishman

[57] ABSTRACT

Perfluoroalkyl-alkyl-sulfide or sulfonyl-alkylene esters of meta- and para-pyromellitates, partially esterified with 3-chloro-1,2-propane diol, of the formulae:

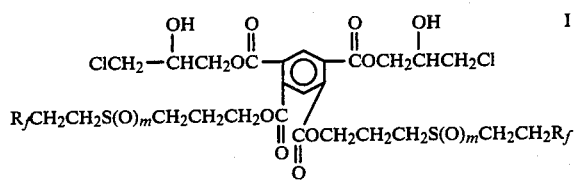

or

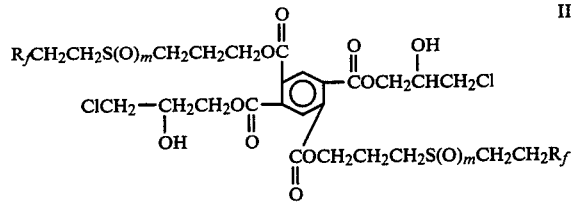

or mixtures thereof, wherein
$R_f$ is perfluoroalkyl of 3 to 18 carbon atoms, and
m is 0 or 2, are useful for incorporation into organic polymers to render them oil repellent and soil resistant.

5 Claims, No Drawings

SULFIDO- AND SULFO-SUBSTITUTED PERFLUOROALKYL PYROMELLITATES

BACKGROUND OF THE INVENTION

This invention relates to perfluoroalkylalkyl (sulfido- or sulfonyl-) alkylene esters of meta- or parapyromellitates partially esterified with 3-chloro-1,2-propane diol and their compositions and use to impart water and oil repellency to synthetic polyesters, such as polyethylene terephthalate, and to synthetic polyamides, such as nylon 6 or nylon 66, especially fibers of such synthetic materials, and to render the same soil resistant.

Certain fluorinated esters of pyromellitates are known and described in U.S. Pat. Nos. 4,209,610, 4,283,292 and 4,317,736. However, such compounds are devoid, for example, of the sulfido or sulfonyl linking moiety of the present compounds.

In addition, since the soil resistant imparting pyromellitate derivatives are characteristically applied to the fiber at elevated temperatures and the resulting treated fiber is annealed at high temperatures, the thermal stability of such pyromellitate derivatives is of critical importance.

It has now unexpectedly been found that the instant pyromellitate derivatives, particularly those containing sulfone groups, exhibit superior thermal stability.

It is thus an object of the present invention to provide pyromellitate derivatives possessing valuable oil repellant and soil resistant properties.

It is yet a further object of the present invention to provide a method of imparting oil repellant and soil resistant properties on synthetic fibrous substrates by applying an effective oil repellant and soil resistant amount of the instant pyromellitate derivatives to such substrate.

These and other objects of the instant invention are described in the following detailed disclosure and examples.

DETAILED DESCRIPTION OF THE INVENTION

The instant invention is directed to novel perfluoroalkyl-alkyl-sulfide or sulfonyl-alkylene esters of meta- and para-pyromellitates, partially esterified with 3-chloro-1,2-propane diol, of the formulae:

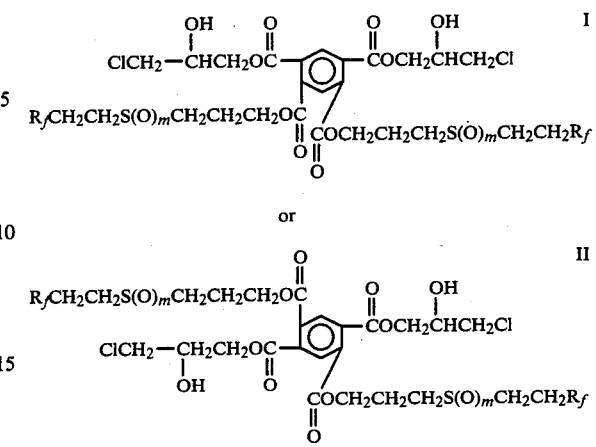

or mixtures thereof, wherein
$R_f$ is perfluoroalkyl of 3 to 18 carbon atoms, and
m is 0 or 2.

Preferably $R_f$ is straight chain perfluoroalkyl of 6 to 12 carbon atoms. Mixtures of such perfluoroalkyl groups are often advantageous.

Preferably, m is 2.

The compounds of the instant invention can be prepared by methods known, per se, in the art.

For example, the compounds of formula I and II where m is 0 or 2 may be prepared by reacting the corresponding alcohols of formula IIIa or IIIb, respectively,

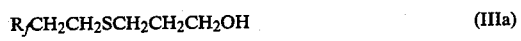

where $R_f$ is previously defined, with pyromellitic dianhydride (PMDA) to form the respective corresponding intermediate diacid/diesters of formulae IV and V

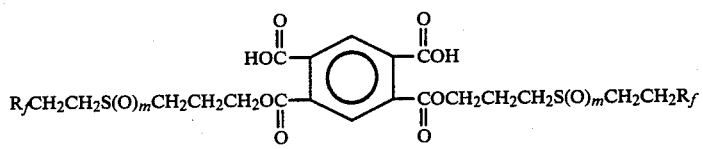

or

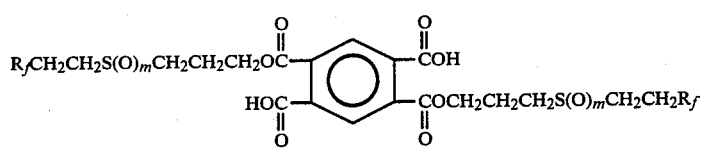

or mixtures thereof, and these intermediate diacid/diesters are then reacted with epichlorohydrin.

Specifically, the products of formulae IV and V are produced by reaction of two moles of fluorinated alcohol with each mole of PMDA to form the diacid/diester. Each mole of the diacid/diester of formula IV and V are then reacted with two moles of epichlorohydrin to produce the product of formula I and II. Because the epoxide may react at the one or two carbon, the product will normally contain minor amounts of material with HOCH$_2$CH(CH$_2$Cl)O(O)C— (the product with a pendant primary alcohol) as well as major amounts of material with HOCH(CH$_2$Cl)CH$_2$)(O)C—(the product with a pendant secondary alcohol).

The diester-diacids represented by structures (IV) and (B) above depict the meta- and para-isomers. It should be appreciated that the diester/diacid intermediate will actually constitute a mixture of the meta- and para-isomers. It is not necessary to isolate the diester-diacid before proceeding to the next step or steps of this invention. However, the diester-diacid may be isolated if desired to do so, by fractional crystallization.

Following production of the diester-diacid intermediate, the third reactant, epichlorohydrin, is added to the reaction medium. The epoxide will react with the free acid moieties of the diester-diacid intermediate to produce a pyromellitate tetraester having two fluorinated ester moieities and two ester moieties having a primary of secondary alcohol. Production of the ester moiety having a primary or secondary alcohol results from the reaction of the oxirane compound at the 1 or 2 carbon with a free acid group.

The reaction between the alcohol of formula IIIa or IIIb and pyromellitic anhydride to form the intermediate products of formulae IV and V, as well as the reaction of these intermediate products with epichlorohydrin to form the compounds of formula I and II, are advantageously conducted in the presence of an inert organic solvent.

Illustrative examples of useful solvents include dimethylformamide, N-methylpyrrolidone and aliphatic esters having a boiling point below about 150° C., such as methyl acetate, ethyl acetate, propyl acetate, etc. Other suitable solvents include aliphatic ketones such as methyl isobutyl ketone. The preferred solvent for the practice of this invention is N-methylpyrrolidone.

The reaction between the alcohol of formula IIIa or IIIb and pyromellitic anhydride to form the intermediates of formulae IV and V is advantageously conducted at a reaction temperature between about 20° C. and about 80° C., preferably between about 40° C. and 70° C. The reaction time can vary widely depending upon reaction temperature, but is generally between about 2 hours and about 40 hours. To accelerate the rate of reaction, a conventional basic catalyst, such as a tertiary amine, including pyridine or a tri(lower alkyl)amine, especially triethylamine, can be employed.

The reaction between the intermediates of formula IV and V and the epichlorohydrin is advantageously conducted at a reaction temperature between about 20° C. to about 90° C., preferably between about 40° C. and about 60° C., for a period of time between about 2 and about 20 hours, preferably in the presence of a conventional basic catalyst, such as a tertiary amine, including pyridine or a tri(loweralkyl)amine, such as tributylamine and especially triethylamine.

If desired, the process comprising the reaction between the alcohol of formula IIIa or IIIb and PMDA, and the reaction between the resulting reaction products of formula IV and V with epichlorohydrin to form the desired products of formulae I and II can be conducted sequentially in the same reaction vessel.

It is desirable to conduct the aforementioned process of this invention in a dry atmosphere, as for example in the presence of dry nitrogen. Pressure is not critical, with atmospheric pressure being suitable. Solvent amounts are not critical, with sufficient solvent being enough to keep at least half of the pyromellitates and fluoroalcohols in solution, since precipitate can redissolve into solution as it reacts. Preferably all of the reactants, intermediates, and products are in solution.

Once formed, the mixtures of the present invention may be recovered from the solvent. Thus, for example, the entire reaction mixture may be added to a non-solvent such as water when N-methylpyrrolidone is used as solvent, or, alternatively, a volatile ester or ketone solvent may be distilled from the reaction mixture. In either case, it is preferred to wash the initial product at least once with water in order to remove any remaining solvent and/or catalyst and/or unreacted reactants, such as unreacted epichlorohydrin.

The product may then be applied to the polyamide or polyester fiber from an organic solvent such as acetone, methanol or dioxane. However, the product can be applied to fibers in the form of an aqueous emulsion e.g. as described in U.S. Pat. No. 4,283,292. The compounds may further be applied to the fiber along with other fiber treating agents, such as conventional spin finishes used to reduce friction of the fiber during processing.

Suitable fibers include poly(caproamide) (nylon 6), poly(hexamethylene diamine adipate) (nylon 66) and other polyamides of both the poly(amino acid) type and poly(diamine dicarboxylate) types such as poly(hexamethylene diamine sebacate), known as nylon 6, 12. Also suitable are polyester such as poly(ethylene terephthalate) (PET). Levels of application are not critical, with levels on a fluorine/fiber basis of 0.075–0.25% fluorine being suitable.

Subsequent to fiber application, it is preferred that the treated fiber be annealed to improve the adherance of the treating agent to the fiber. Annealing temperatures lie between about 80° and about 160° C. The mixtures of the present invention are especially advantageous in that fibers treated with the mixtures of formula I and II exhibit excellent soil resistance properties and retention of these properties. The annealing step may preferably be conducted at temperatures between about 100° C. and about 140° C.

The thermal stability of the subject pyromellitates of formulas I and II, containing sulfone groups in particular, is better than pyromellitates derived from perfluoroalkyethanols. As shown hereinafter, the char yield is higher, indicating improved thermal stability and improved fire resistance for the subject finishes.

The pyromellitates of the present invention have extremely high resistance to soiling, and soil resistant properties imparted to fibers are retained by the fibers after numerous laundering cycles. Therefore, fibers treated with the compounds of the present invention will retain soil resistance properties for long period of time in actual use environments.

The following Examples are for illustrative purposes only and are not intended to restrict the scope of the instant invention. All parts are by weight unless otherwise indicated.

EXAMPLE 1

Pyromellitic dianhydride (2.2 g, 0.01 moles) a fluorinated alcohol of the formula C$_8$F$_{17}$(CH$_2$)$_2$SO$_2$(CH$_2$)$_3$OH (11.4 g, 0.02 moles), dimethylaminopyridine (0.02 g) and butyl acetate (50 g) were mixed under nitrogen and the reaction mixture was stirred at 60° C. for 24 hours. The solvent was evaporated under reduced pressure to give 12.4 g (91% yield) of a mixture containing

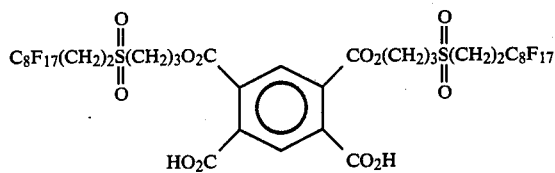

and

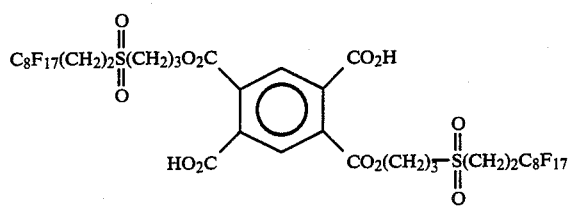

in equal proportions.

| N.M.R. data: | | |
|---|---|---|
| 2.02 ppm | Broad Complex | O=C—O—CH$_2$C$\underline{H}_2$—CH$_2$—SO$_2$ |
| 2.77 ppm | Broad Complex | C$_8$F$_{17}$—C$\underline{H}_2$ |
| 3.32 ppm | Complex | C$\underline{H}_2$—SO$_2$ |
| 4.41 ppm | Triplet | O=COC$\underline{H}_2$ |
| 7.94 ppm | Complex | Aromatics |

EXAMPLE 2

Following the procedure from example 1 and using fluoroalcohol R$_f$CH$_2$CH$_2$OH (wherein R$_f$ is C$_6$F$_{13}$, C$_8$F$_{17}$ and C$_{10}$F$_{21}$ in ratios of 1:2:1) a mixture containing

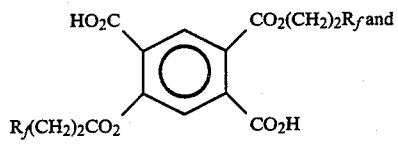

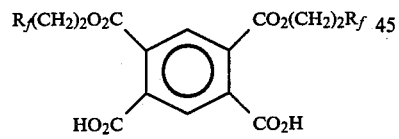

in equal proportions was obtained in 97% yield.

| N.M.R. data: | | |
|---|---|---|
| 2.55 ppm | Complex | R$_f$—C$\underline{H}_2$— |
| 4.35 & 4.59 ppm | Triplets | O=C—O—C$\underline{H}_2$ |
| 7.93 & 8.04 ppm | Singlets | Aromatics |

EXAMPLE 3

The diacid mixture obtained from example 1 (21.4 g, 0.016 moles), N-methyl Pyrollidone (150 g), epichlorohydrin (8.7 g, 0.095 moles) and triethyl amine (0.02 g) were allowed to react for six hours at 60°.

The dark solution was poured into water and a solid precipitated and was collected by filtration (93% yield). The solid was found to be an equimolar mixture of

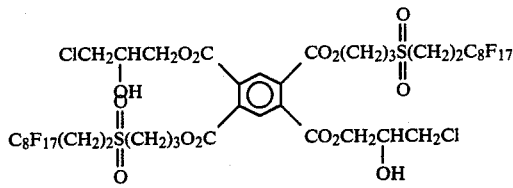

and

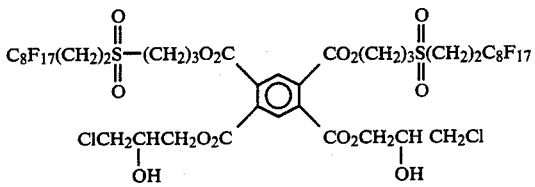

| N.M.R. data: | | |
|---|---|---|
| 1.92 & 2.19 ppm | Multiplet(s) | O—CH—C$\underline{H}_2$—CH$_2$—S(O$_2$) (and —S?) |
| 2.69 ppm | Complex | C$_8$F$_{17}$—C$\underline{H}_2$— |
| 3.41–3.64 ppm | Complex | C$_8$F$_{17}$—CH$_2$—C$\underline{H}_2$—S(O$_2$)—C$\underline{H}_2$— |
| 4.34–4.41 ppm | Complex | O=C—O—C$\underline{H}_2$— |
| 7.82–8.61 ppm | Complex | Aromatics |

In like manner, the product of Example 2 is converted to the corresponding epichlorohydrin reaction product of Formulae I and II.

EXAMPLE 4

Pyromellitic dianhydride (2.2 g, 0.01 moles), a fluorinated alcohol C$_8$F$_{17}$(CH$_2$)$_2$S(CH$_2$)$_3$OH (10.2 g, 0.02 moles), N-methyl Pyrollidone (120 g), epichlorohydrin (7.2 g, 0.08 moles) and triethyl amine (0.04 g) were mixed under nitrogen and the reaction mixture was stirred at 60° for 72 hours. The resulting dark brown solution was poured into water (800 ml) and the beige solid that precipitated was collected by filtration. The solid was found to be an equimolar mixture of

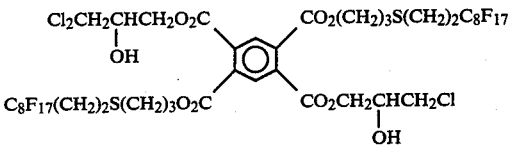

and

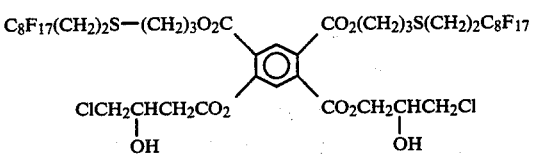

| M.M.R. data: | | |
|---|---|---|
| 2.05 ppm | Multiplet | O—CH—C$\underline{H}_2$—CH$_2$—S— |
| 2.37 ppm | Complex | C$_8$F$_{17}$—C$\underline{H}_2$— |
| 2.71 ppm | Complex | C$_8$F$_{17}$—CH$_2$—C$\underline{H}_2$—S—C$\underline{H}_2$— |
| 4.16 ppm | Qunitet | —C($\underline{H}$)(OH)— |
| 4.47 ppm | Complex | O=C—O—C$\underline{H}_2$— |
| 8.07 ppm | Complex | Aromatics |

EXAMPLE 5

Following the procedure from example 4

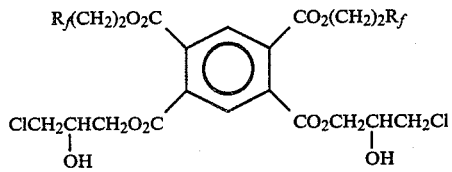

and

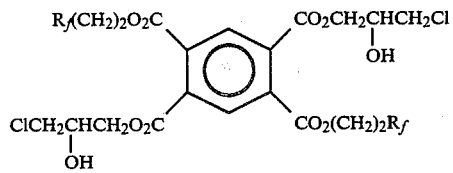

wherein $R_f$ is $C_6F_{13}$, $C_8F_{17}$ and $C_{10}F_{21}$ in ratios 1:2:1, where synthesized in 92% yield.

EXAMPLE 6

As the compounds of the invention will be utilized for textile and carpet treatment it is desirable that they exhibit reduced flammability. The residue left after thermal degradation of the compound (char yield) is a measure of its flammability. The char yield was determined by thermogravimetric analysis. (10° C./min., 10 ml $N_2$/min., 80% suppression.) Results are summarized in the table below.

| Compound from Example | Char Yield at 400° C. (% of original weight) |
| --- | --- |
| 3 | 12 |
| 5 | 6 |

EXAMPLE 7

The compound from Example 4 was screened as a carpet finish in a series of carpet walk-on tests. The compound was spray-applied from methyl ethyl ketone to white tufted nylon carpet at 0.175% F on the carpet weight. The following table summarizes the test results:

TABLE 1

| | Carpet Walk-on Tests - Spray Application | | | | Hold-out** | |
| | Walk-on Test* | | | | 10% i-PrOH | Olive |
| Sample Applied | 1 weeks | 2 weeks | 3 weeks | 4 weeks | in water | Oil |
| --- | --- | --- | --- | --- | --- | --- |
| Untreated Control | 2–3 | 2 | 2 | 2 | — | — |
| Example 4 | 4 | 3–4 | 3–4 | 3–4 | + | + |
| Total Step Count | 1910 | 3366 | 4466 | 7036 | | |

*visual dry-soil ratings on white nylon carpet
1 = poor, attracts a lot of soil - even more than untreated
2 = fair
3 = good
4 = very good
5 = excellent, nearly the same as new, un-walked on carpet
**Resistance of initially treated carpet to above liquids, drops applied.
+ = beaded up
− = soaked in

What is claimed is:

1. A compound of the formula

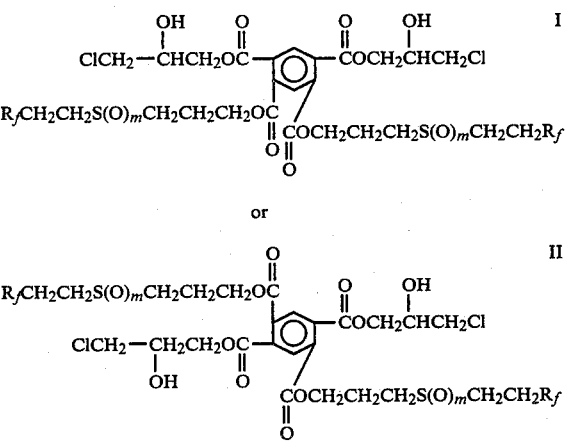

or a mixture thereof, wherein $R_f$ is perfluoroalkyl of 3 to 18 carbon atoms, and m is 0 or 2.

2. A compound according to claim 1, wherein $R_f$ is straight chain perfluoroalkyl of 6 to 12 carbon atoms, or a mixture thereof.

3. A compound according to claim 1, wherein m is 0.

4. A compound according to claim 2, wherein m is 0.

5. A method of imparting oil repellant and soil resistant properties on a synthetic polyamide or polyester fibrous substrate by contacting said fibrous substrate with an effective oil repellant and soil resistant imparting amount of a compound according to claim 1.

* * * * *